United States Patent
Li

(10) Patent No.: US 10,679,757 B2
(45) Date of Patent: Jun. 9, 2020

(54) METHOD AND APPARATUS FOR ESTABLISHING A BLOOD PRESSURE MODEL AND METHOD AND APPARATUS FOR DETERMINING A BLOOD PRESSURE

(71) Applicant: BOE Technology Group Co., Ltd., Beijing (CN)

(72) Inventor: Hui Li, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 335 days.

(21) Appl. No.: 15/680,365

(22) Filed: Aug. 18, 2017

(65) Prior Publication Data
US 2018/0075209 A1 Mar. 15, 2018

(30) Foreign Application Priority Data
Sep. 14, 2016 (CN) .......................... 2016 1 0824575

(51) Int. Cl.
*A61B 5/00* (2006.01)
*G16H 50/50* (2018.01)
(Continued)

(52) U.S. Cl.
CPC ............. *G16H 50/50* (2018.01); *A61B 5/021* (2013.01); *A61B 5/0205* (2013.01);
(Continued)

(58) Field of Classification Search
CPC ...... G16H 50/50; A61B 5/021; A61B 5/0402; A61B 5/02125; A61B 5/0245
See application file for complete search history.

(56) References Cited

U.S. PATENT DOCUMENTS

2008/0039731 A1 2/2008 McCombie et al.
2008/0262362 A1* 10/2008 Kolluri .............. A61B 5/02125
600/490
(Continued)

FOREIGN PATENT DOCUMENTS

| CN | 102008296 A | 4/2011 |
| CN | 102186411 A | 9/2011 |

(Continued)

OTHER PUBLICATIONS

Determinants of Radial Artery Pulse Wave Analysis in Asymptomatic Individuals, by Duprez et al. (Year: 2004).*
(Continued)

*Primary Examiner* — Gary Jackson
*Assistant Examiner* — Zahed Kabir
(74) *Attorney, Agent, or Firm* — Westman, Champlin & Koehler, P.A.

(57) ABSTRACT

The embodiments of the present disclosure disclose a method and apparatus for establishing a blood pressure model. The method comprises: acquiring pulse wave data, electrocardiographic data, blood pressure data and body mass indexes of a plurality of subjects to be examined; determining pulse wave transit time and pulse wave intensity ratios based on the pulse wave data and the electrocardiographic data; establishing a blood pressure model based on the blood pressure data, the pulse wave transit time, the pulse wave intensity ratios, and/or the body mass index.

20 Claims, 7 Drawing Sheets

(51) Int. Cl.
*A61B 5/0245* (2006.01)
*A61B 5/021* (2006.01)
*G16H 50/30* (2018.01)
*G16H 40/63* (2018.01)
*A61B 5/0205* (2006.01)
*A61B 5/0402* (2006.01)
*A61B 5/024* (2006.01)

(52) U.S. Cl.
CPC .......... *A61B 5/0245* (2013.01); *A61B 5/0402* (2013.01); *A61B 5/7235* (2013.01); *A61B 5/7278* (2013.01); *G16H 40/63* (2018.01); *G16H 50/30* (2018.01); *A61B 5/024* (2013.01); *A61B 5/02125* (2013.01)

(56) References Cited

U.S. PATENT DOCUMENTS

| | | |
|---|---|---|
| 2011/0196244 A1 | 8/2011 | Ribas Ripoll et al. |
| 2012/0065525 A1* | 3/2012 | Douniama ......... A61B 5/02116 600/485 |
| 2016/0081572 A1* | 3/2016 | Hong ................... A61B 5/6898 600/301 |
| 2016/0213266 A1* | 7/2016 | Fuke ................... A61B 5/0004 |
| 2017/0109495 A1 | 4/2017 | Xin |
| 2017/0258340 A1* | 9/2017 | Przybyszewski .. A61B 5/02141 |
| 2017/0347895 A1* | 12/2017 | Wei ...................... A61B 5/0205 |

FOREIGN PATENT DOCUMENTS

| | | | |
|---|---|---|---|
| CN | 102397064 A | * | 4/2012 |
| CN | 102397064 A | | 4/2012 |
| CN | 103976721 A | | 8/2014 |
| CN | 104856661 A | | 8/2015 |
| CN | 104873186 A | | 9/2015 |
| WO | WO-2017024457 A1 | * | 2/2017 ............. A61B 5/021 |

OTHER PUBLICATIONS

Pulse wave analysis by Michael F. O'Rourke, Alfredo Pauca and Xiong-Jing Jiang (Year: 2001).*

First Office Action, including Search Report, for Chinese Patent Application No. 201610824575.4, dated Jul. 14, 2017, 11 pages.

* cited by examiner

METHOD AND APPARATUS FOR ESTABLISHING A BLOOD PRESSURE MODEL AND METHOD AND APPARATUS FOR DETERMINING A BLOOD PRESSURE

CROSS-REFERENCE TO RELATED APPLICATION(S)

This application claims priority to the Chinese Patent Application No. 201610824575.4, filed on Sep. 14, 2016, entitled "METHOD AND APPARATUS FOR ESTABLISHING A BLOOD PRESSURE MODEL AND METHOD AND APPARATUS FOR DETERMINING A BLOOD PRESSURE," which is incorporated herein by reference in its entirety.

TECHNICAL FIELD

The present disclosure relates to blood pressure modeling, and more particularly, to a method and apparatus for establishing a blood pressure model and a method and apparatus for determining a blood pressure of a subject to be examined by using the established blood pressure model.

BACKGROUND

With the richness of material life and the resulting increase in average life span, the number of hypertensive patients also increases in modern society. Obviously, it is very important to comprehend historic blood pressure values and blood pressure trends for daily prevention and treatment of hypertension. Therefore, a blood pressure value needs to be frequently measured.

However, the existing methods for measuring a blood pressure are mainly auscultation-based and oscillometry-based methods, both of which require one to wear an inflatable cuff and apply pressures on artery blood vessels to obtain blood pressure values, which cannot avoid discomfort caused by an increased pressure due to air inflation.

Currently, it has been put forward that there is a correlation between pulse wave transit time and a blood pressure during a period of time for a certain individual. Therefore, a corresponding blood pressure model may be established. However, this correlation varies with individuals. Thus, such a blood pressure model is only applicable to a particular individual but is not applicable to a group which comprises a large number of individuals.

SUMMARY

In order to at least partially solve or alleviate the above problems, the embodiments of the present disclosure provide a method and apparatus for establishing a blood pressure model and a method and apparatus for determining a blood pressure of a subject to be examined by using a blood pressure model.

According to an aspect of the present disclosure, there is provided a method for establishing a blood pressure model. The method comprises: acquiring pulse wave data, electrocardiographic data, blood pressure data and body mass indexes of a plurality of subjects to be examined, wherein the blood pressure data comprises systolic blood pressure data and diastolic blood pressure data. Further, the method comprises: determining pulse wave transit time and pulse wave intensity ratios based on the pulse wave data and the electrocardiographic data; establishing a systolic blood pressure model indicative of a relationship between systolic blood pressures and the pulse wave transit time and the body mass indexes based on the systolic blood pressure data, the pulse wave transit time and the body mass index; and establishing a diastolic blood pressure model indicative of a relationship between diastolic blood pressures and the pulse wave intensity ratios and the body mass indexes based on the diastolic blood pressure data, the pulse wave intensity ratios, and the body mass indexes. Here, the blood pressure model comprises (but is not limited to) the systolic blood pressure model and the diastolic blood pressure model.

In the embodiments of the present disclosure, the method further comprises: acquiring ages and/or genders of the plurality of subjects to be examined. Further, the method comprises: establishing a systolic blood pressure model indicative of a relationship between the systolic blood pressures and the pulse wave transit time, the body mass indexes and the ages and/or genders based on the systolic blood pressure data, the pulse wave transit time, the body mass indexes and the ages and/or genders of the plurality of subjects to be examined; and establishing a diastolic blood pressure model indicative of a relationship between the diastolic blood pressures and the pulse wave intensity ratios, the body mass indexes and the ages and/or genders based on the diastolic blood pressure data, the pulse wave intensity ratios, the body mass indexes and the ages and/or genders of the plurality of subjects to be examined.

In the embodiments of the present disclosure, the method further comprises: acquiring ages and/or genders of the plurality of subjects to be examined. Further, the method comprises: dividing the plurality of subjects to be examined into a plurality of groups based on the ages and/or genders; for each of the plurality of groups, establishing a systolic blood pressure model for the group indicative of a relationship between systolic blood pressures and pulse wave transit time and body mass indexes of subjects to be examined included in the group based on systolic blood pressure data, the pulse wave transit time and the body mass indexes; and for each of the plurality of groups, establishing a diastolic blood pressure model for the group indicative of a relationship between diastolic blood pressures and pulse wave intensity ratios, and body mass indexes of subjects to be examined included in the group based on diastolic blood pressure data, the pulse wave intensity ratios and the body mass indexes.

In the embodiments of the present disclosure, establishing a systolic blood pressure model comprises: constructing a first training set comprising the systolic blood pressure data, the pulse wave transit time and the body mass indexes of the plurality of subjects to be examined; and determining parameters in the systolic blood pressure model by using the first training set with the pulse wave transit time and the body mass indexes being inputs of the systolic blood pressure model and the systolic blood pressure data being an output of the systolic blood pressure model.

In the embodiments of the present disclosure, establishing a diastolic blood pressure model comprises: constructing a second training set comprising the diastolic blood pressure data, the pulse wave intensity ratios and the body mass indexes of the plurality of subjects to be examined; and determining parameters in the diastolic blood pressure model by using the second training set with the pulse wave intensity ratios and the body mass indexes being inputs of the diastolic blood pressure model and the diastolic blood pressure data being an output of the diastolic blood pressure model.

In the embodiments of the present disclosure, the parameters are determined by using a least square regression method.

In the embodiments of the present disclosure, the method further comprises: constructing a first test set comprising systolic blood pressure data, pulse wave transit time and body mass indexes of other subjects to be examined; calculating systolic blood pressure data by using the systolic blood pressure model with the pulse wave transit time and the body mass indexes in the first test set; and evaluating the systolic blood pressure model based on the calculated systolic blood pressure data and the systolic blood pressure data in the first test set.

In the embodiments of the present disclosure, the method further comprises: constructing a second test set comprising diastolic blood pressure data, pulse wave intensity ratios and body mass indexes of other subjects to be examined; calculating diastolic blood pressure data by using the diastolic blood pressure model with the pulse wave intensity ratios and the body mass indexes in the second test set; and evaluating the diastolic blood pressure model based on the calculated diastolic blood pressure data and the diastolic blood pressure data in the second test set.

According to another aspect of the present disclosure, there is provided a method for determining a blood pressure of a subject to be examined. The method comprises: acquiring pulse wave data, electrocardiographic data and a body mass index of the subject to be examined. Further, the method comprises: determining pulse wave transit time and a pulse wave intensity ratio based on the pulse wave data and the electrocardiographic data; and determining the blood pressure of the subject to be examined according to a pre-established blood pressure model based on the pulse wave transit time, the pulse wave intensity ratio and the body mass index. In the embodiments of the present disclosure, the method further comprises: acquiring an age and/or gender of the subject to be examined; and determining the blood pressure of the subject to be examined according to a pre-established blood pressure model based on the pulse wave transit time, the pulse wave intensity ratio, the body mass index and the age and/or gender.

In the embodiments of the present disclosure, the method further comprises: acquiring an age and/or gender of the subject to be examined; selecting a blood pressure model suitable for the subject to be examined from a plurality of pre-established blood pressure models according to the age and/or gender; and determining the blood pressure of the subject to be examined according to the selected blood pressure model based on the pulse wave transit time, the pulse wave intensity ratio and the body mass index.

In the embodiments of the present disclosure, the blood pressure model is established in accordance with the method for establishing a blood pressure model described above.

According to another aspect of the present disclosure, there is provided an apparatus for establishing a blood pressure model. The apparatus comprises a data acquisition module, a data processing module and a model establishment module. The data acquisition module is configured to acquire pulse wave data, electrocardiographic data, body mass indexes and blood pressure data of a plurality of subjects to be examined, wherein the blood pressure data comprises systolic blood pressure data and diastolic blood pressure data. The data processing module is configured to determine pulse wave transit time and pulse wave intensity ratios based on the pulse wave data and the electrocardiographic data; and the model establishment module comprises a systolic blood pressure model establishment module and a diastolic blood pressure model establishment module, wherein the systolic blood pressure model establishment module is configured to establish a systolic blood pressure model indicative of a relationship between systolic blood pressures and the pulse wave transit time and the body mass indexes based on the systolic blood pressure data, the pulse wave transit time and the body mass index; and the diastolic blood pressure model establishment module is configured to establish a diastolic blood pressure model indicative of a relationship between diastolic blood pressures and the pulse wave intensity ratios and the body mass indexes based on the diastolic blood pressure data, the pulse wave intensity ratios, and the body mass indexes. Here, the systolic blood pressure model and the diastolic blood pressure model constitute the blood pressure model.

In the embodiments of the present disclosure, the data acquisition module is further configured to acquire ages and/or genders of the plurality of subjects to be examined; the systolic blood pressure model establishment module is further configured to establish a systolic blood pressure model indicative of a relationship between the systolic blood pressures and the pulse wave transit time, the body mass indexes and the ages and/or genders based on the systolic blood pressure data, the pulse wave transit time, the body mass indexes and the ages and/or genders; and the diastolic blood pressure model establishment module is further configured to establish a diastolic blood pressure model indicative of a relationship between the diastolic blood pressures and the pulse wave intensity ratios, the body mass indexes and the ages and/or genders based on the diastolic blood pressure data, the pulse wave intensity ratios, the body mass indexes and the ages and/or genders.

In the embodiments of the present disclosure, the data acquisition module is further configured to acquire ages and/or genders of the plurality of subjects to be examined. The apparatus further comprises a grouping module configured to divide the plurality of subjects to be examined into a plurality of groups based on the ages and/or genders; the systolic blood pressure model establishment module is further configured to: for each of the plurality of groups, establish a systolic blood pressure model for the group indicative of a relationship between systolic blood pressures and pulse wave transit time and body mass indexes of subjects to be examined included in the group based on systolic blood pressure data, the pulse wave transit time and the body mass indexes; and the diastolic blood pressure model establishment module is further configured to: for each of the plurality of groups, establish a diastolic blood pressure model for the group indicative of a relationship between diastolic blood pressures and pulse wave intensity ratios, and body mass indexes of subjects to be examined included in the group based on diastolic blood pressure data, the pulse wave intensity ratios and the body mass indexes.

In the embodiments of the present disclosure, when a systolic blood pressure model is established, the systolic blood pressure model establishment module comprises a first training set unit configured to construct a first training set comprising the systolic blood pressure data, the pulse wave transit time and the body mass indexes of the plurality of subjects to be examined; and a parameter determination unit configured to determine parameters in the systolic blood pressure model by using the first training set with the pulse wave transit time and the body mass indexes being inputs of the systolic blood pressure model and the systolic blood pressures being an output of the systolic blood pressure model.

In the embodiments of the present disclosure, the diastolic blood pressure model establishment module comprises a second training set unit configured to construct a second training set comprising the diastolic blood pressure data, the pulse wave intensity ratios and the body mass indexes of the plurality of subjects to be examined; and a parameter determination unit configured to determine parameters in the diastolic blood pressure model by using the second training set with the pulse wave intensity ratios and the body mass indexes being inputs of the diastolic blood pressure model and the diastolic blood pressures being an output of the diastolic blood pressure model.

In the embodiments of the present disclosure, the systolic blood pressure model establishment module or the diastolic blood pressure model establishment module is configured to determine the parameters by using a least square regression method.

In the embodiments of the present disclosure, the apparatus further comprises a systolic blood pressure model evaluation module, which comprises a first test set unit configured to construct a first test set comprising other systolic blood pressure data, other pulse wave transit time and other body mass indexes; a first test calculation unit configured to calculate systolic blood pressure data by using the systolic blood pressure model with the pulse wave transit time and the body mass indexes in the first test set; and a first test evaluation unit configured to evaluate the systolic blood pressure model based on the calculated systolic blood pressure data and the systolic blood pressure data in the first test set.

In the embodiments of the present disclosure, the apparatus further comprises a diastolic blood pressure model evaluation module, which comprises a second test set unit configured to construct a second test set comprising diastolic blood pressure data, pulse wave intensity ratios and body mass indexes of other subjects to be examined; a second test calculation unit configured to calculate diastolic blood pressure data by using the diastolic blood pressure model with the pulse wave intensity ratios and the body mass indexes in the second test set; and a second test evaluation unit configured to evaluate the diastolic blood pressure model based on the calculated diastolic blood pressure data and the diastolic blood pressure data in the second test set.

According to another aspect of the present disclosure, there is provided an apparatus for determining a blood pressure of a subject to be examined. The apparatus comprises a pulse wave acquisition module, an electrocardiographic data acquisition module, a body mass index acquisition module, a data processing module and a blood pressure determination module. The pulse wave acquisition module is configured to acquire pulse wave data of the subject to be examined, the electrocardiographic data acquisition module is configured to acquire electrocardiographic data of the subject to be examined; the body mass index acquisition module is configured to acquire a body mass index of the subject to be examined; the data processing module is configured to determine pulse wave transit time and a pulse wave intensity ratio based on the pulse wave data and the electrocardiographic data; and the blood pressure determination module is configured to determine the blood pressure of the subject to be examined according to a pre-established blood pressure model based on the pulse wave transit time, the pulse wave intensity ratio and the body mass index.

In the embodiments of the present disclosure, the apparatus further comprises: an age and gender acquisition module, configured to acquire an age and/or gender of the subject to be examined; wherein the blood pressure determination module is further configured to determine the blood pressure of the subject to be examined according to a pre-established blood pressure model based on the pulse wave transit time, the pulse wave intensity ratio, the body mass index and the age and/or gender.

In the embodiments of the present disclosure, the apparatus further comprises an age and gender acquisition module configured to acquire an age and/or gender of the subject to be examined; and a model selection module configured to select a blood pressure model suitable for the subject to be examined from a plurality of pre-established blood pressure models according to the age and/or gender; wherein the blood pressure determination module is further configured to determine the blood pressure of the subject to be examined according to the selected blood pressure model based on the pulse wave transit time, the pulse wave intensity ratio and the body mass index.

In the embodiments of the present disclosure, the apparatus further comprises an update module configured to acquire a new blood pressure model from a remote server and replace a current blood pressure model with the new blood pressure model.

In the embodiments of the present disclosure, the apparatus further comprises a pulse wave sensor coupled to the pulse wave acquisition module and configured to measure a pulse wave of the subject to be examined; and an electrocardiogram sensor coupled to the electrocardiographic data acquisition module and configured to measure an electrocardiogram of the subject to be examined.

In the embodiments of the present disclosure, the blood pressure model is established by the apparatus for establishing a blood pressure model described above.

According to another aspect of the present disclosure, there is provided an apparatus for establishing a blood pressure model, comprising: a processor; a memory configured to store instructions that, when executed by the processor, cause the processor to: acquire pulse wave data, electrocardiographic data, body mass indexes and blood pressure data of a plurality of subjects to be examined; determine pulse wave transit time and pulse wave intensity ratios based on the pulse wave data and the electrocardiographic data; and establishing the blood pressure model based on one or more of the blood pressure data, the pulse wave transit time, the pulse wave intensity ratios, and the body mass indexes of the plurality of subjects to be examined.

In the embodiments of the present disclosure, the blood pressure data comprises systolic blood pressure data and diastolic blood pressure data, and the instructions, when executed by the processor, further cause the processor to: establish a systolic blood pressure model indicative of a relationship between systolic blood pressures and the pulse wave transit time and the body mass indexes based on the systolic blood pressure data, the pulse wave transit time and the body mass index of the plurality of subjects to be examined, and establish a diastolic blood pressure model indicative of a relationship between diastolic blood pressures and the pulse wave intensity ratios and the body mass indexes based on the diastolic blood pressure data, the pulse wave intensity ratios and the body mass indexes of the plurality of subjects to be examined, wherein the blood pressure model comprises the systolic blood pressure model and the diastolic blood pressure model.

In the embodiments of the present disclosure, the instructions, when executed by the processor, further cause the processor to: acquire ages and/or genders of the plurality of subjects to be examined; establish a systolic blood pressure model indicative of a relationship between the systolic blood pressures and the pulse wave transit time, the body mass indexes and the ages and/or genders based on the systolic blood pressure data, the pulse wave transit time, the body mass indexes and the ages and/or genders of the plurality of subjects to be examined; and establish a diastolic blood pressure model indicative of a relationship between the diastolic blood pressures and the pulse wave intensity ratios, the body mass indexes and the ages and/or genders based on the diastolic blood pressure data, the pulse wave intensity ratios, the body mass indexes and the ages and/or genders of the plurality of subjects to be examined.

In the embodiments of the present disclosure, the instructions, when executed by the processor, further cause the processor to: acquire ages and/or genders of the plurality of subjects to be examined; divide the plurality of subjects to be examined into a plurality of groups based on the ages and/or genders; for each of the plurality of groups, establish a systolic blood pressure model for the group indicative of a relationship between systolic blood pressures and pulse wave transit time and body mass indexes of subjects to be examined included in the group based on systolic blood pressure data, the pulse wave transit time and the body mass indexes; and for each of the plurality of groups, establish a diastolic blood pressure model for the group indicative of a relationship between diastolic blood pressures and pulse wave intensity ratios, and body mass indexes of subjects to be examined included in the group based on diastolic blood pressure data, the pulse wave intensity ratios and the body mass indexes.

In the embodiments of the present disclosure, the instructions, when executed by the processor, further cause the processor to: construct a first training set comprising the systolic blood pressure data, the pulse wave transit time and the body mass indexes of the plurality of subjects to be examined; and determine parameters in the systolic blood pressure model by using the first training set with the pulse wave transit time and the body mass indexes being inputs of the systolic blood pressure model and the systolic blood pressure data being an output of the systolic blood pressure model; and/or, the instructions, when executed by the processor, further cause the processor to: construct a second training set comprising the diastolic blood pressure data, the pulse wave intensity ratios and the body mass indexes of the plurality of subjects to be examined; and determine parameters in the diastolic blood pressure model by using the second training set with the pulse wave intensity ratios and the body mass indexes being inputs of the diastolic blood pressure model and the diastolic blood pressure data being an output of the diastolic blood pressure model.

In the embodiments of the present disclosure, the instructions, when executed by the processor, further cause the processor to: construct a first test set comprising systolic blood pressure data, pulse wave transit time and body mass indexes of other subjects to be examined; calculate systolic blood pressure data by using the systolic blood pressure model with the pulse wave transit time and the body mass indexes in the first test set; and evaluate the systolic blood pressure model based on the calculated systolic blood pressure data and the systolic blood pressure data in the first test set; and/or, the instructions, when executed by the processor, further cause the processor to: construct a second test set comprising diastolic blood pressure data, pulse wave intensity ratios and body mass indexes of other subjects to be examined; calculate diastolic blood pressure data by using the diastolic blood pressure model with the pulse wave intensity ratios and the body mass indexes in the second test set; and evaluate the diastolic blood pressure model based on the calculated diastolic blood pressure data and the diastolic blood pressure data in the second test set.

According to another aspect of the present disclosure, there is provided an apparatus for determining a blood pressure of a subject to be examined, comprising: a processor; a memory configured to store instructions that, when executed by the processor, cause the processor to acquire pulse wave data, electrocardiographic data and a body mass index of the subject to be examined; determine pulse wave transit time and a pulse wave intensity ratio based on the pulse wave data and the electrocardiographic data; and determine the blood pressure of the subject to be examined according to a pre-established blood pressure model based on the pulse wave transit time, the pulse wave intensity ratio and the body mass index.

In the embodiments of the present disclosure, the instructions, when executed by the processor, further cause the processor to: acquire an age and/or gender of the subject to be examined; and determine the blood pressure of the subject to be examined according to a pre-established blood pressure model based on the pulse wave transit time, the pulse wave intensity ratio, the body mass index and the age and/or gender.

In the embodiments of the present disclosure, the instructions, when executed by the processor, further cause the processor to: acquire an age and/or gender of the subject to be examined; select a blood pressure model suitable for the subject to be examined from a plurality of pre-established blood pressure models according to the age and/or gender; and determine the blood pressure of the subject to be examined according to the selected blood pressure model based on the pulse wave transit time, the pulse wave intensity ratio and the body mass index.

In the embodiments of the present disclosure, the instructions, when executed by the processor, further cause the processor to: acquire a new blood pressure model from a remote server and replace a current blood pressure model with the new blood pressure model.

BRIEF DESCRIPTION OF THE DRAWINGS

The above and other features and advantages of the exemplary embodiments will become more apparent from the following detailed description of the exemplary embodiments with reference to the accompanying drawings. The accompanying drawings are intended to illustrate exemplary embodiments and should not be construed as limiting the expected scope of the claims. Unless expressly stated otherwise, the accompanying drawings are not considered to be drawn to scale.

DETAILED DESCRIPTION

Figure 1:
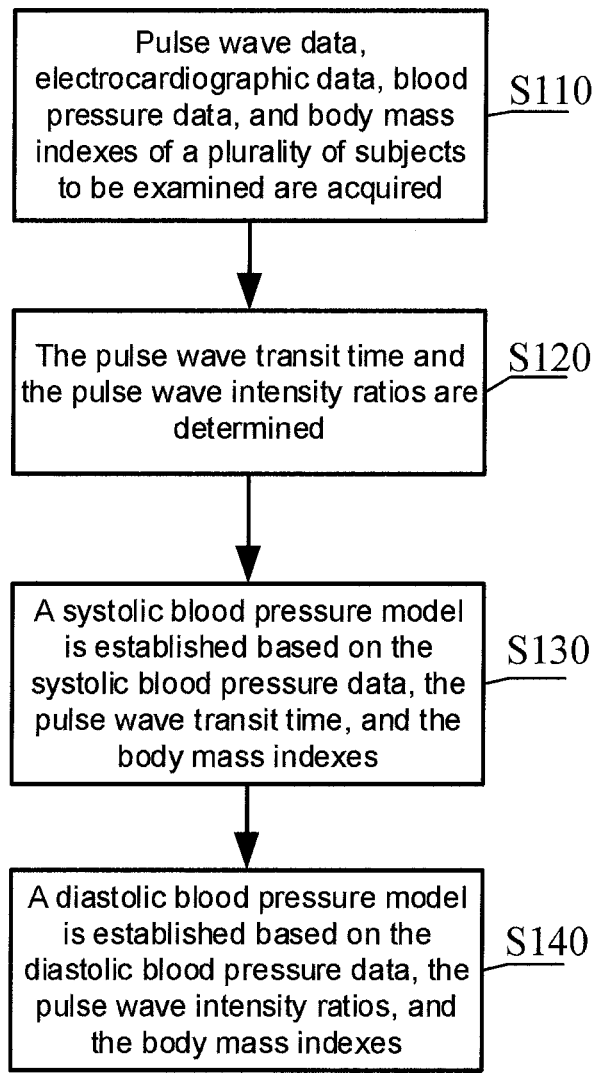
FIG. 1 illustrates a flowchart of a method for establishing a blood pressure model according to an exemplary embodiment of the present disclosure.

Although the exemplary embodiments support various modifications and alternatives, embodiments thereof are shown by way of example in the accompanying drawings and will be described in detail here. It is to be understood, however, that the present disclosure is not intended to be limited to the particular forms disclosed, but rather, the present disclosure encompasses all modifications, equivalents, and alternatives falling within the scope of the claims. The same numerals always refer to the same elements throughout the description of the accompanying drawings.

Before the exemplary embodiments are discussed in more detail, it is noted that some exemplary embodiments are described as processors or methods are depicted as flowcharts. Although operations are described as being processed sequentially in the flowcharts, many operations may be performed concurrently, simultaneously or synchronously. In addition, the order of the operations can be rearranged. The processes may be terminated when the operations thereof are completed, but may also have additional steps which are not included in the figures. The processes may correspond to methods, functions, procedures, subroutines, subprograms etc.

The methods discussed below (some of which are illustrated by the flowcharts) may be implemented by hardware, software, firmware, middleware, pseudo-codes, hardware description language, or any combination thereof. When implemented in software, firmware, middleware, or pseudo-codes, program codes or code segments used to perform the necessary tasks may be stored in a machine or computer readable medium, for example a storage medium, such as a non-transient storage medium. (Multiple) processors may perform the necessary tasks.

The specific structural and functional details disclosed here are merely representative for the purpose of describing exemplary embodiments. The present disclosure, however, may be embodied in many alternatives and should not be construed as only being limited to the embodiments set forth here.

It will be understood that although the terms "first" and "second" are used here to describe various elements, these elements should not be limited by these terms. These terms are used only to distinguish one element from another. For example, a first element may be referred to as a second element, and similarly, the second element may be referred to as the first element without departing from the scope of the present disclosure. As used herein, the term "and/or" comprises any and all combinations of one or more of the listed associated items.

It will be understood that when an element is referred to as being "connected" or "coupled" to another element, it can be directly connected or coupled to the other element, or there may be an intermediate element therebetween. As a comparison, when an element is referred to as being "directly connected" or "directly coupled" to another element, there is no intermediate element therebetween. Other words used to describe a relationship between elements should be interpreted in the same way (for example, "between" relative to "directly between", "adjacent" relative to "directly adjacent", etc.).

The terms are used here for the purpose of describing specific embodiments only and are not intended to be limiting of exemplary embodiments. As used herein, the singular forms "a", "an" and "the" are intended to include a plural form, unless the context clearly dictates otherwise. It is to be understood that, when used herein, the terms "comprising" "comprise", "including" and/or "include" refer to the presence of the mentioned features, integers, steps, operations, elements and/or components, but do not preclude the presence or addition of one or more other features, integers, steps, operations, elements, components, and/or groups thereof.

It should also be noted that, in some alternative embodiments, the mentioned functions/actions may occur in an order other than that mentioned in the figures. For example, depending on the functions/actions involved, two figures shown in succession may actually be executed at the same time or may sometimes be executed in a reverse order.

Unless otherwise defined, all terms (including technical and scientific terms) used herein have the same meaning as commonly understood by one of ordinary skill in the art to which the exemplary embodiments belong. It will be further understood that the terms defined in, for example, the commonly used dictionaries should be interpreted as having the meanings consistent with those in an environment in the related art and should not be interpreted in an idealized or excessive formal meaning, unless it is explicitly defined here.

A plurality of portions of the exemplary embodiments and corresponding detailed description are given in a form of software or arithmetic and symbolic representations of operations performed on data bits in a computer memory. These descriptions and representations are those by which those skilled in the art have effectively conveyed the essence of their works to other skilled in the art. As the terms used herein, and as commonly used, algorithms are considered to be self-consistent sequences that lead to desired results. Steps are those that require physical manipulation of physical quantities. In general, although this is not necessarily the case, these quantities are in a form of optical, electrical or magnetic signals that can be stored, transmitted, combined, compared, and otherwise manipulated. It has been proved many times that it is convenient to refer to these signals as bits, values, elements, symbols, characters, terms, numbers, etc., in principle for general use.

In the following description, illustrative embodiments will be described with reference to (for example, in a form of flowchart) symbolic representations of actions and operations. The above operations may be implemented as program modules or functional processes, including performing specific tasks or implementing routines, programs, objects, components, data structures, etc. in a specific abstraction data type, and may be implemented by using existing hardware at existing network components. Such existing hardware may comprise one or more Central Processing Units (CPUs), Digital Signal Processors (DSPs), application specific integrated circuits, Field Programmable Gate Array (FPGA) computers, etc.

It should be borne in mind, however, that all such and similar terms are associated with appropriate physical quantities and are merely convenient signs applied to these quantities. Unless otherwise particularly indicated in other ways, or as apparent from the present disclosure, the terms, such as "processing", "calculating", "computing", "determining" or "displaying" etc., refer to actions and processes for manipulating data which is expressed as physical and electronic quantities in a register and a memory in a computer system and converting the data into other data by the computer system or a similar electronic computing device. The other data is similarly expressed as physical quantities in the memory or the register of the computer system or other such information storage, transmission or display device.

It is also noted that aspects of exemplary embodiments of software implementations are typically encoded on some forms of program storage media or implemented on some types of transmission media. The program storage medium may be any non-transient storage medium, for example magnetic (such as floppy or hard disk) or optical (such as compact disk read only memory or "CD ROM"), and may be read-only or randomly accessed. Similarly, the transmission medium may be a twisted pair, a coaxial cable, an optical fiber, or some other suitable transmission medium known in the art. The exemplary embodiments are not limited by these aspects of any given embodiment.

Before the embodiments of the present disclosure are described in detail, the regression analysis and the Pulse Wave-Blood Pressure (PTT-BP) group model are described first.

The regression analysis is the core of statistics, and as a generalized concept, it generally refers to methods which use one or more predictive variables (also known as independent variables or explanatory variables) to predict response variables (also known as dependent variables, criterion variables or outcome variables). In general, the regression analysis may be used to select explanatory variables related to the response variables to describe a relationship therebetween, or to generate an equation to predict response variables through the explanatory variables.

The Ordinary Least Square (OLS for short) regression method comprises simple linear regression, polynomial regression and multi-linear regression. OLS regression is to predict quantized dependent variables by predicting a weighted sum of variables, where weights are parameters obtained through data estimation. An OLS regression fitting model is in a form of:

$$Y_i = \beta_0 + \beta_1 X_{1i} + \ldots \beta_k X_{ki} (i=1 \ldots n)$$

where n is a number of observations and k is a number of predictive variables. $Y_i$ is a predicted value of a dependent variable corresponding to an $i^{th}$ observation, $X_{ij}$ is a value of a $j^{th}$ predictive variable corresponding to an $i^{th}$ observation, $\beta_0$ is an intercept term, and $\beta_j$ is a regression coefficient of the $j^{th}$ predictive variable.

In order to be able to properly interpret the coefficients of the OLS model, the data must meet the following statistical assumptions:

normality: for fixed values of the predictive variables, the dependent variables are in a normal distribution;
independence: $Y_i$ values are independent of each other;
linearity: the dependent variables and the predictive variables are linearly correlated; and
homogeneity of variances: the variances of the dependent variables do not vary with the levels of the predictive variables.

Changes in blood pressure may be divided into high-frequency (0.2-0.35 Hz) changes and low-frequency (0.1-0.15 Hz) changes. A pulse wave is formed by broadcasting a pulse (vibration) of a heart to an outer circumference along arteries and blood flows. Pulse Transit Time (PTT for short) may reflect the influences of respiration on changes in blood pressure, which correspond to changes in blood pressure in a high frequency range, and Photoplethysmogram (PPG for short) Intensity Ratio (PIR for short) may reflect changes in diameter of blood vessels and movements of the blood vessels, which correspond to changes in blood pressure in a low frequency range. Therefore, theoretically the PTT and the PIR are important characteristic values which reflect a Blood Pressure (BP). It was found through experiments that a correlation between a Systolic blood pressure (SBP for short) and the PTT is high, and a correlation between a diastolic blood pressure (DBP for short) and the PIR is high. Therefore, when a model is established, the PTT is mainly considered for the SBP, and the PIR is mainly considered for the DBP. When a model is established for a group, corresponding models are established for different groups, and ages, genders, heights, weights, etc. may be impact factors.

The exemplary embodiments will be described in detail below with reference to the accompanying drawings. FIG. 1 illustrates a flowchart of a method for establishing a blood pressure model according to an exemplary embodiment. As shown in FIG. 1, according to an embodiment of the present disclosure, in step S110, pulse wave data, electrocardiographic data, blood pressure data and body mass indexes of a plurality of subjects to be examined are acquired, wherein the blood pressure data comprises systolic blood pressure data and diastolic blood pressure data. In the embodiment of the present disclosure, the subject to be examined is a person. It will be appreciated by those skilled in the art that the subject to be examined may also be an animal. In an embodiment, the pulse wave data may be acquired, for example, by a pulse wave sensor, such as a photoelectric sensor. In another embodiment, the pulse wave data may be acquired through direct input. In an embodiment, the electrocardiographic data may be acquired, for example, via an electrocardiogram sensor, such as a dry electrode. In another embodiment, the electrocardiographic data may also be acquired through direct input. In an embodiment, the blood pressure data may be acquired through direct input. In an embodiment, the blood pressure data may be measured by a blood pressure measurement device. In an embodiment, the body mass indexes may be acquired through direct input. In an embodiment, the body mass indexes may also be calculated by acquiring a height and a weight of the subjects to be examined. A Body Mass Index (BMI) is a square of a weight (W) of a subject to be examined divided by a height (L) of the subject to be examined, wherein the weight is in kilograms and the height is in meters.

In step S120, the pulse wave transit time and the pulse wave intensity ratios are determined based on the acquired pulse wave data and electrocardiographic data. In an embodiment, the pulse wave data comprises time of a maximum slope point of a pulse wave, a peak value of the pulse wave, and a trough value of the pulse wave, and the electrocardiographic data comprises time of a peak of an electrocardiogram. In this embodiment, the pulse wave transit time is calculated according to the time of the maximum slope point of the pulse wave and the time of the peak of the electrocardiogram. Specifically, the pulse wave transit time is a difference between the time of the maximum slope point of the pulse wave and the time of the peak of the electrocardiogram. In an embodiment, the pulse wave data comprises time of a maximum slope point of a pulse wave, a peak value of the pulse wave, and a trough value of the pulse wave, and the electrocardiographic data comprises time of a peak of an electrocardiogram. In this embodiment, the pulse wave intensity ratio is calculated according to the peak value and the valley value of the pulse wave, and specifically the pulse wave intensity ratio is a ratio of the peak value of the pulse wave to the valley value of the pulse wave.

In step S130, a systolic blood pressure model indicative of a relationship between systolic blood pressures and the pulse wave transit time and the body mass indexes is established based on the systolic blood pressure data, the pulse wave transit time and the body mass indexes.

Figure 4:
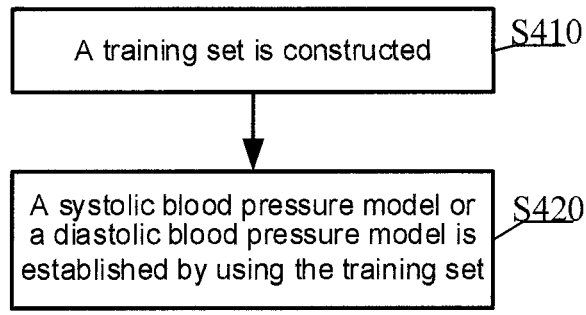
FIG. 4 illustrates a flowchart of a method for establishing a systolic blood pressure model or a diastolic blood pressure model according to an exemplary embodiment of the present disclosure.

In an embodiment of the present disclosure, as shown in FIG. 4, establishing a systolic blood pressure model comprises the following steps. In step 410, a training set is constructed, wherein the training set comprises the systolic blood pressure data, the pulse wave transit time and the body mass indexes of the plurality of subjects to be examined. Then, in step 420, parameters in the systolic blood pressure model are determined by using the training set with the pulse wave transit time and the body mass indexes being inputs of the systolic blood pressure model and the systolic blood pressures being an output of the systolic blood pressure model. In an embodiment, systolic blood pressure regression parameters are determined through regression analysis by combining the pulse wave transit time and the body mass indexes of the plurality of subjects to be examined with the systolic blood pressure data of the plurality of subjects to be examined. In an embodiment, the systolic blood pressure regression parameters may be determined by using a least square regression method.

In an embodiment, the systolic blood pressure model may be expressed as:

$$SBP = a1 \times PTT + a2 \times PTT^2 + a3 \times BMI + a4 \times BMI^2 + a5 \quad \text{(equation 1)}$$

wherein SBP is a systolic blood pressure, PTT is pulse wave transit time, BMI is a body mass index, and a1, a2, a3, a4 and a5 are systolic blood pressure regression parameters.

In step S140, a diastolic blood pressure model indicative of a relationship between diastolic blood pressures and the pulse wave intensity ratios and the body mass indexes is established based on the diastolic blood pressure data, the pulse wave intensity ratios and the body mass indexes.

In an embodiment of the present disclosure, as shown in FIG. 4, establishing a diastolic blood pressure model comprises the following steps. In step S410, a training set is constructed, wherein the training set comprises the diastolic blood pressure data, the pulse wave intensity ratios and the body mass indexes of the plurality of subjects to be examined. Further, in step S420, parameters in the diastolic blood pressure model are determined by using the training set with the pulse wave intensity ratios and the body mass indexes being inputs of the diastolic blood pressure model and the diastolic blood pressures being an output of the diastolic blood pressure model. In an embodiment, diastolic blood pressure regression parameters are determined through regression analysis by combining the pulse wave intensity ratios and the body mass indexes of the plurality of subjects to be examined with the diastolic blood pressure data of the plurality of subjects to be examined. In an embodiment, the diastolic blood pressure regression parameters may be determined by using a least square regression method.

In an embodiment, the diastolic blood pressure model may be expressed as:

$$DBP = b1 \times PIR + b2 \times PIR^2 + b3 \times BMI + b4 \times BMI^2 + b5 \quad \text{(equation 2)}$$

wherein DBP is a diastolic blood pressure, PIR is a pulse wave intensity ratio, BMI is a body mass index, and b1, b2, b3, b4 and b5 are diastolic blood pressure regression parameters.

Figure 2:
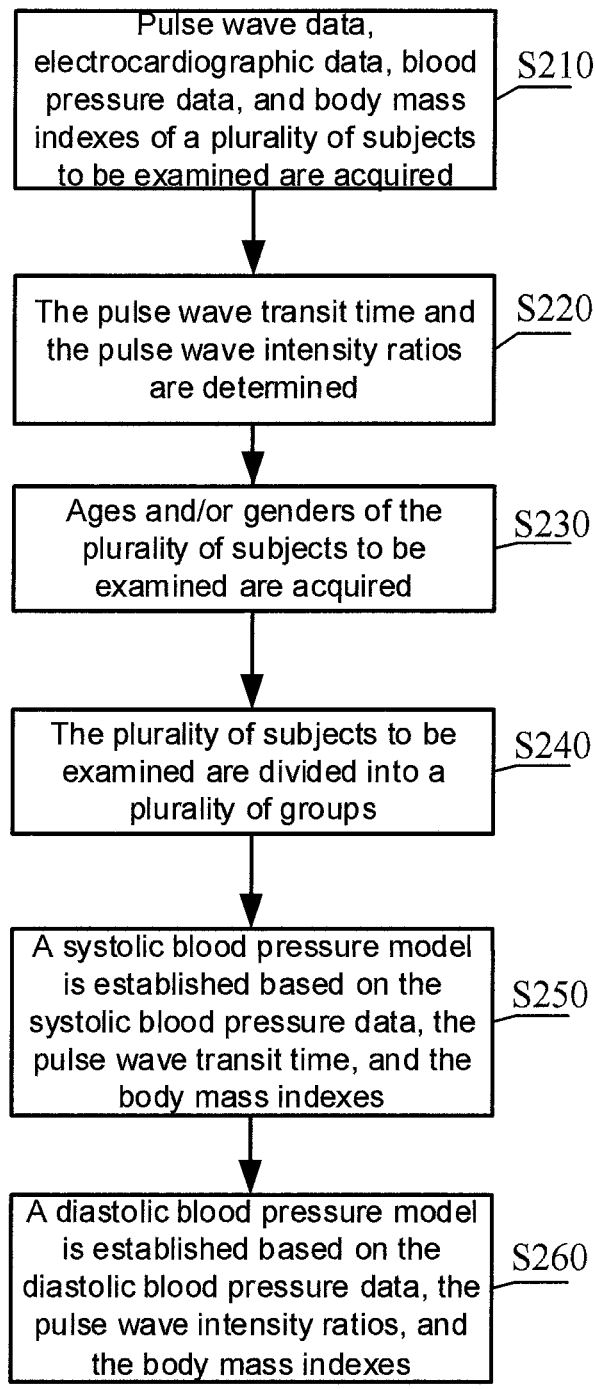
FIG. 2 illustrates a flowchart of a method for establishing a blood pressure model according to another exemplary embodiment of the present disclosure.

FIG. 2 illustrates another exemplary embodiment of the present disclosure, wherein steps S210-S220 are the same as steps S110-120 shown in FIG. 1. Further, the method disclosed in this embodiment further comprises, in step S320, acquiring ages and/or genders of the plurality of subjects to be examined.

Further, in step S240, the plurality of subjects to be examined are divided into a plurality of groups based on the ages and/or genders of the plurality of subjects to be examined. For example, the plurality of subjects to be examined may be divided into two groups based on genders. For example, it is also possible to divide the plurality of subjects to be examined based on ages, for example, the plurality of subjects to be examined are grouped every 10 years old, i.e., objects from 0 to 10 years old are divided into a group, objects from 11 to 20 years old are divided into a group, and so on. Similarly, the plurality of subjects to be examined may also be grouped every 5 years old. In an embodiment, the plurality of subjects to be examined may be divided by combining ages and genders, for example, the plurality of subjects to be examined are classified based on genders and then are grouped every 5 years old.

Further, for each divided group, steps S250 and S260 are performed to generate a systolic blood pressure model and a diastolic blood pressure model for each group, where steps S250 and S260 are the same as steps S130 and S140 shown in FIG. 1, and will not be repeated here.

It should be noted that although steps S210-S260 are described here in a sequential manner, it is not intended to limit the execution order. In fact, at least a part of the steps described may be performed in a different order, or in parallel with other steps, for example, step S230 may be performed before step S210 or S220 or in parallel with step S210 or S220.

Figure 3:
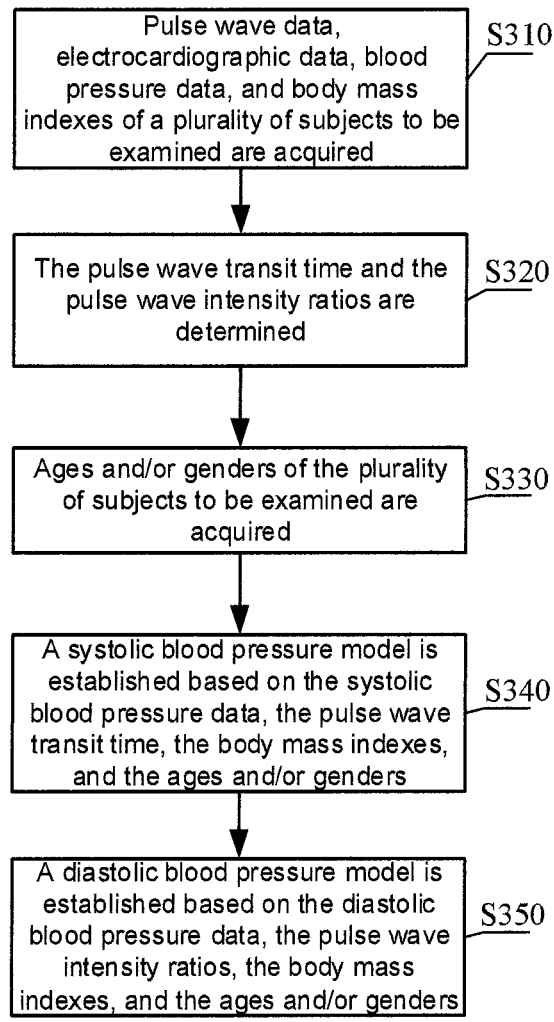
FIG. 3 illustrates a flowchart of a method for establishing a blood pressure model according to yet another exemplary embodiment of the present disclosure.

FIG. 3 illustrates yet another exemplary embodiment of the present disclosure, wherein steps S310-S320 are the same as steps S110-120 shown in FIG. 1. In addition, the method further comprises, in step S330, acquiring ages and/or genders of the plurality of subjects to be examined.

Further, in step S340, a systolic blood pressure model indicative of a relationship between systolic blood pressures and pulse wave transit time, body mass indexes and ages and/or genders is established based on the systolic blood pressure data, the pulse wave transit time, the body mass indexes and the ages and/or genders.

In an embodiment of the present disclosure, as shown in FIG. 4, establishing a systolic blood pressure model comprises the following steps. In step 410, a training set is constructed, wherein the training set comprises the systolic blood pressure data, the pulse wave transit time, the body mass indexes and the ages and/or genders of the plurality of subjects to be examined. Then, in step 420, parameters in the systolic blood pressure model are determined by using the training set with the pulse wave transit time, the body mass indexes and the ages and/or genders being inputs of the systolic blood pressure model and the systolic blood pressures being an output of the systolic blood pressure model.

In an embodiment, systolic blood pressure regression parameters are determined through regression analysis by combining the pulse wave transit time, the body mass indexes and the ages and/or genders of the plurality of subjects to be examined with the systolic blood pressure data of the plurality of subjects to be examined. In an embodiment, the systolic blood pressure regression parameters may be determined by using a least square regression method.

In an embodiment, the systolic blood pressure model may be expressed as:

$$SBP = a1 \times PTT + a2 \times PTT^2 + a3 \times BMI + a4 \times BMI^2 + a5 \times AGE + a6 \times AGE^2 + a7 \quad \text{(equation 3)}$$

wherein SBP is a systolic blood pressure, PTT is pulse wave transit time, BMI is a body mass index, AGE is an age, and a1, a2, a3, a4, a5, a6 and a7 are systolic blood pressure regression parameters.

Further, in step S340, a diastolic blood pressure model indicative of a relationship between diastolic blood pressures and pulse wave intensity ratios, body mass indexes and ages and/or genders is established based on the diastolic blood pressure data, the pulse wave intensity ratios, the body mass indexes and the ages and/or genders.

In an embodiment of the present disclosure, as shown in FIG. 4, establishing a diastolic blood pressure comprises the following steps. In step S410, a training set is constructed, wherein the training set comprises the diastolic blood pressure data, the pulse wave intensity ratios, the body mass indexes and the ages and/or genders of the plurality of subjects to be examined. Further, in step S420, parameters in the diastolic blood pressure model are determined by using the training set with the pulse wave intensity ratios, the body mass indexes and the ages and/or genders being inputs of the diastolic blood pressure model and the diastolic blood pressures being an output of the diastolic blood pressure model. In an embodiment, diastolic blood pressure regression parameters are determined through regression analysis by combining the pulse wave intensity ratios, the body mass indexes and the ages and/or genders of the plurality of subjects to be examined with the diastolic blood pressure data of the plurality of subjects to be examined. In an embodiment, the diastolic blood pressure regression parameters may be determined by using a least square regression method.

In an embodiment, the diastolic blood pressure model may be expressed as:

$$DBP = b1 \times PIR + b2 \times PIR^2 + b3 \times BMI + b4 \times BMI^2 + b5 \times AGE + b6 \times AGE^2 + b7 \quad \text{(equation 4)}$$

wherein DBP is a diastolic blood pressure, PIR is a pulse wave intensity ratio, BMI is a body mass index, AGE is an age, and b1, b2, b3, b4, b5, b6 and b7 are diastolic blood pressure regression parameters.

In an embodiment of the present disclosure, the method further comprises constructing a test set comprising systolic blood pressure data, pulse wave transit time and body mass indexes of other subjects to be examined. Then, systolic blood pressure data is calculated by using the systolic blood pressure model with the pulse wave transit time and the body mass indexes in the test set. Next, the systolic blood pressure model is evaluated based on the calculated systolic blood pressure data and the systolic blood pressure data in the test set.

It should be noted that although steps S310-S350 are described here in a sequential manner, it is not intended to limit the execution order. In fact, at least a part of the steps described may be performed in a different order, or in parallel with other steps, for example, step S330 may be performed before step S310 or S320 or in parallel with step S310 or S320.

In an embodiment of the present disclosure, the method further comprises constructing a test set comprising diastolic blood pressure data, pulse wave intensity ratios and body mass indexes of other subjects to be examined. Then, diastolic blood pressure data is calculated by using the diastolic blood pressure model with the pulse wave intensity ratios and the body mass indexes in the test set. Next, the diastolic blood pressure model is evaluated based on the calculated diastolic blood pressure data and the diastolic blood pressure data in the test set.

It is possible to check whether a difference between the calculated blood pressure data of the subject to be examined by using a model and actual blood pressure data of the subject to be examined is within an allowable error range by evaluating the model by using a test set.

With the embodiments disclosed in the present disclosure, the systolic blood pressure model and the diastolic blood pressure model can be established with higher accuracy. Obviously, according to the embodiments disclosed in the present disclosure, independent variables used to establish the systolic blood pressure model or the diastolic blood pressure model are not limited to the pulse wave data, the electrocardiographic data or the body mass indexes, and any index which may distinguish between different categories of people may be applied to the methods disclosed in the present disclosure.

Figure 5:
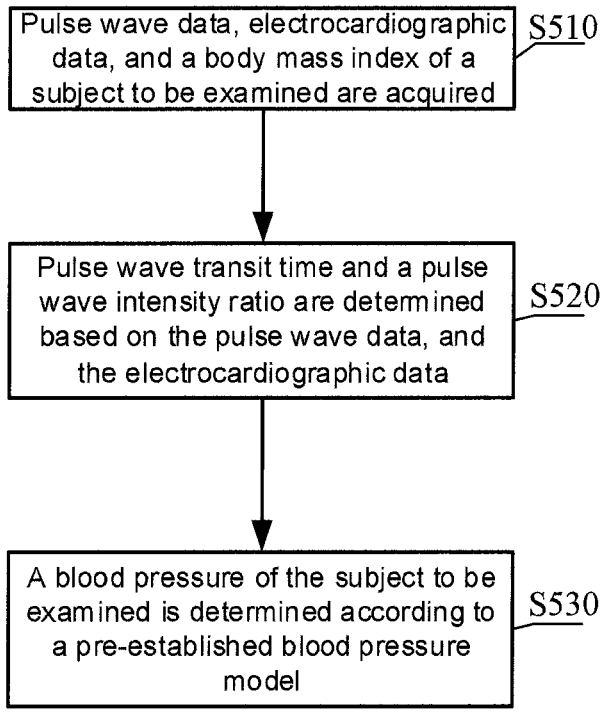
FIG. 5 illustrates a flowchart of a method for determining a blood pressure of a subject to be examined according to an exemplary embodiment of the present disclosure.

FIG. 5 illustrates a flowchart of a method for determining a blood pressure of a subject to be examined according to an exemplary embodiment. As shown in FIG. 5, according to an embodiment of the present disclosure, pulse wave data, electrocardiographic data, and a body mass index of the subject to be examined are acquired in step S510. The pulse wave data, the electrocardiographic data and the body mass index may be manually input by the subject to be examined or an operator, or may also be measured by a measurement device.

In step S520, pulse wave transit time and a pulse wave intensity ratio are determined based on the pulse wave data and the electrocardiographic data. In an embodiment, the pulse wave data comprises time of a maximum slope point of a pulse wave, a peak value of the pulse wave and a trough value of the pulse wave, and the electrocardiographic data comprises time of a peak of an electrocardiogram. In this embodiment, the pulse wave transit time is calculated according to the time of the maximum slope point of the pulse wave and the time of the peak of the electrocardiogram. Specifically, the pulse wave transit time is a difference between the time of the maximum slope point of the pulse wave and the time of the peak of the electrocardiogram. In an embodiment, the pulse wave data comprises time of a maximum slope point of a pulse wave, a peak value of the pulse wave and a trough value of the pulse wave, and the electrocardiographic data comprises time of a peak of an electrocardiogram. In this embodiment, the pulse wave intensity ratio is calculated according to the peak value and the valley value of the pulse wave, and specifically the pulse wave intensity ratio is a ratio of the peak value of the pulse wave to the valley value of the pulse wave.

In step S530, a systolic blood pressure and a diastolic blood pressure of the subject to be examined are calculated respectively according to a pre-established blood pressure model based on the pulse wave transit time, the pulse wave intensity ratio and the body mass index. The pre-established blood pressure model is, for example, the systolic blood pressure model and/or diastolic blood pressure model established in steps S130 and S140 disclosed above, such as equations 1 and 2 shown above. Obviously, the systolic blood pressure and the diastolic blood pressure of the subject to be examined can be easily calculated by using equations 1 and 2 based on the pulse wave transit time, the pulse wave intensity ratio and the body mass index.

It should be noted that although the calculation of the systolic blood pressure and the diastolic blood pressure of the subject to be examined is described by using the equation associated with the least square regression method here, it is to be understood that the embodiments of the present disclosure are not limited to the use of the parameters obtained by the least square regression method for calculation. Any suitable regression algorithm or other statistical method may be applied to the embodiments of the present disclosure.

Figure 6:
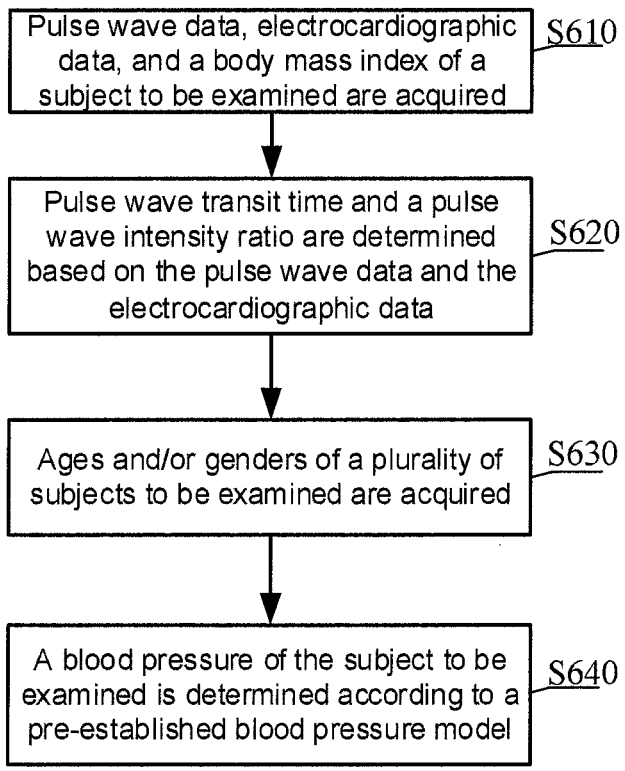
FIG. 6 illustrates a flowchart of a method for determining a blood pressure of a subject to be examined according to another example embodiment of the present disclosure.

FIG. 6 illustrates a method for determining a blood pressure of a subject to be examined according to another embodiment of the present disclosure, wherein steps S610 and S620 are the same as steps S510 and S520 shown in FIG. 5, respectively. Further, the method comprises, in step 630, acquiring ages and/or genders of a plurality of subjects to be examined. In an embodiment, an age and/or gender may, for example, be manually input by the subject to be examined or an operator.

Further, in step S640, a systolic blood pressure and a diastolic blood pressure of the subjects to be examined are calculated according to a pre-established blood pressure model based on the pulse wave transit time, the pulse wave intensity ratio, the body mass index and the age and/or gender. Similarly to step S530, the pre-established blood pressure model is, for example, the systolic blood pressure model and/or diastolic blood pressure model established in steps S340 and S350 disclosed above, such as equations 3 and 4 shown above. Obviously, the systolic blood pressure and the diastolic blood pressure of the subject to be examined can be easily calculated by using equations 3 and 4 based on the pulse wave transit time, the pulse wave intensity ratio, the body mass index and the age.

It should be noted that although steps S610-S640 are described here in a sequential manner, it is not intended to limit the execution order. In fact, at least a part of the steps described may be performed in a different order, or in parallel with other steps, for example, step S630 may be performed before step S610 or S620 or in parallel with step S610 or S620.

Figure 7:
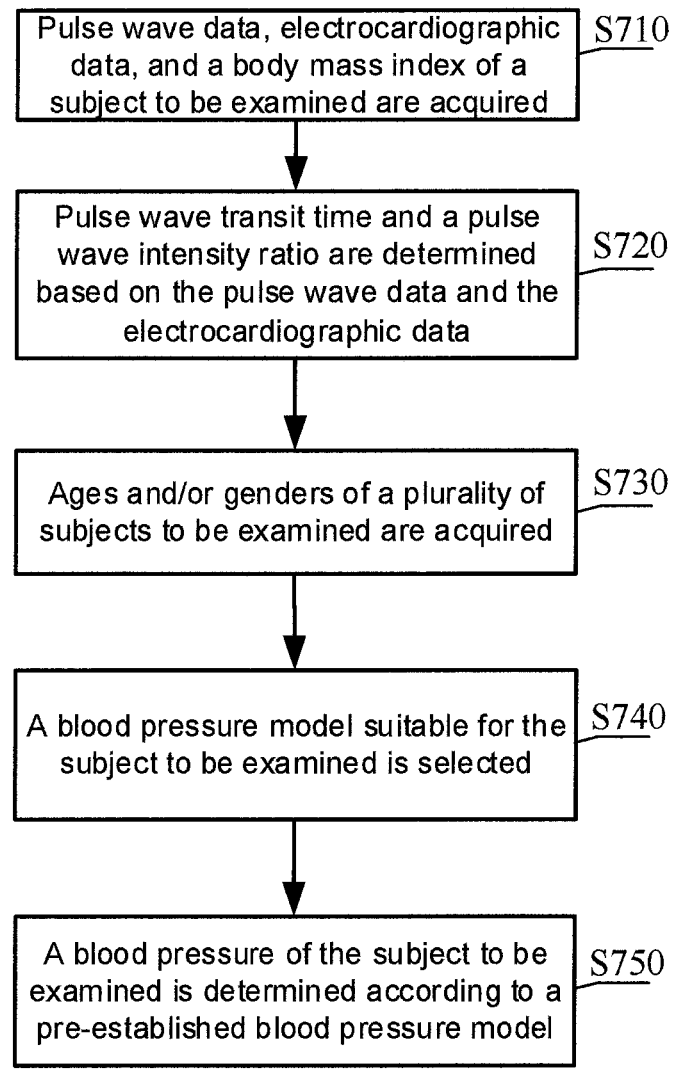
FIG. 7 illustrates a flowchart of a method for determining a blood pressure of a subject to be examined according to yet another exemplary embodiment of the present disclosure.

FIG. 7 illustrates a method for determining a blood pressure of a subject to be examined according to another embodiment of the present disclosure, wherein steps S710, S720 and S730 are the same as steps S610, S620 and S630 shown in FIG. 6, respectively. Further, the method further comprises, in step 740, selecting a blood pressure model from a plurality of pre-established blood pressure models according to on an age and/or gender, wherein the plurality of pre-established blood pressure models are used for a certain age range and/or gender respectively. In the present embodiment, the blood pressure model may be a systolic blood pressure model and/or a diastolic blood pressure model as shown in equation 1 and 2.

In step 750, a systolic blood pressure and a diastolic blood pressure of the subject to be examined are calculated respectively according to the selected blood pressure model based on the pulse wave transit time, the pulse wave intensity ratio and the body mass index. This calculation is similar to the calculation performed in step 530, and will not be described again for the sake of brevity.

Figure 8:
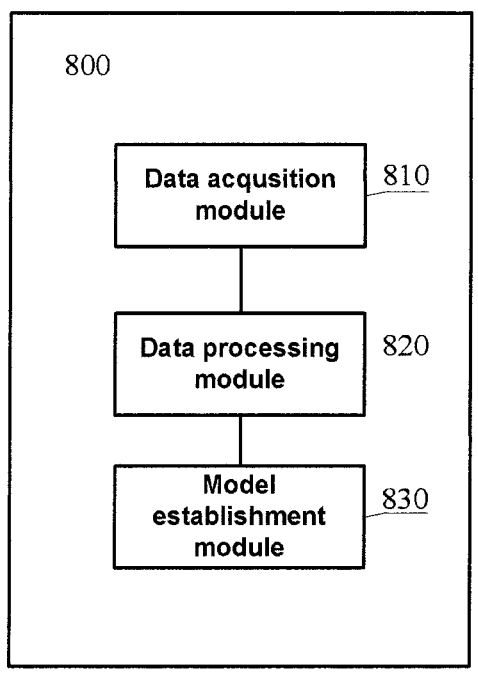
FIG. 8 illustrates a diagram of an apparatus for establishing a blood pressure model according to an exemplary embodiment of the present disclosure.

FIG. 8 illustrates a diagram of an apparatus 800 for establishing a blood pressure model according to an embodiment of the present disclosure. As shown in FIG. 8, according to an embodiment of the present disclosure, the apparatus 800 comprises a data acquisition module 810, a data processing module 820 and a model establishment module 830.

The data acquisition module 810 is configured to acquire pulse wave data, electrocardiographic data, body mass indexes and blood pressure data of a plurality of subjects to be examined, wherein the blood pressure data comprises systolic blood pressure data and diastolic blood pressure data. In an embodiment, the data may be acquired through direct input. In an embodiment, the pulse wave data may be acquired, for example, through a pulse wave sensor coupled to the data acquisition module 810, wherein the pulse wave sensor may be, for example, a photoelectric sensor. In an embodiment, the electrocardiographic data may be acquired, for example, through an electrocardiograph sensor coupled to the data acquisition module 810, wherein the electrocardiograph sensor may, for example, be a dry electrode. In an embodiment, the blood pressure data may be acquired through direct input. In an embodiment, the blood pressure data may be measured by using a blood pressure measurement device coupled to the data acquisition module 510. In an embodiment, the body mass indexes may be input by using an input device coupled to the data acquisition module 810.

The data processing module 820 is configured to determine pulse wave transit time and pulse wave intensity ratios based on the pulse wave data and the electrocardiographic data. In an embodiment, the data processing module 820 is configured to calculate the pulse wave transit time according to time of a maximum slope point of a pulse wave included in the pulse wave data and time of a peak of an electrocardiogram included in the electrocardiographic data. Specifically, the pulse wave transit time is a difference between the time of the maximum slope point of the pulse wave and the time of the peak of the electrocardiogram. In an embodiment, the data processing module 820 is configured to calculate a pulse wave intensity ratio according to a peak value and a valley value of the pulse wave included in the pulse wave data, and specifically the pulse wave intensity ratio is a ratio of the peak value of the pulse wave to the valley value of the pulse wave.

The model establishment module 830 may comprise a systolic blood pressure model establishment module and a diastolic blood pressure model establishment module. The systolic blood pressure model establishment module is configured to establish a systolic blood pressure model indicative of a relationship between systolic blood pressures and the pulse wave transit time and the body mass indexes based on the systolic blood pressure data, the pulse wave transit time and the body mass index. The diastolic blood pressure model establishment module is configured to establish a diastolic blood pressure model indicative of a relationship between diastolic blood pressures and the pulse wave intensity ratios and the body mass indexes based on the diastolic blood pressure data, the pulse wave intensity ratios, and the body mass indexes. Here, the systolic blood pressure model and the diastolic blood pressure model constitute the blood pressure model.

In an embodiment, the systolic blood pressure model establishment module is configured to establish the systolic blood pressure model through regression analysis by combining the pulse wave transit time and the body mass indexes of the plurality of subjects to be examined with the systolic blood pressure data of the plurality of subjects to be examined. In an embodiment, the systolic blood pressure model establishment module is configured to establish the systolic blood pressure model by using a least squares regression method.

In an embodiment, the diastolic blood pressure model establishment module is configured to establish the diastolic blood pressure model through regression analysis by combining the pulse wave intensity ratios and the body mass indexes of the plurality of subjects to be examined with the diastolic blood pressure data of the plurality of subjects to be examined. In an embodiment, the diastolic blood pressure model establishment module is configured to establish the diastolic blood pressure model by using a least squares regression method.

In an embodiment of the present disclosure, the data acquisition module 810 is further configured to acquire ages and/or genders of the plurality of subjects to be examined. In an embodiment, the ages and/or genders of the subjects to be examined are acquired through direct input. In an embodiment, the ages and/or genders of the subjects to be examined are manually input by the subjects to be examined or an operator of the apparatus via an input device coupled to the data acquisition module 810.

The systolic blood pressure model establishment module is further configured to establish a systolic blood pressure model indicative of a relationship between the systolic blood pressures and the pulse wave transit time, the body mass indexes and the ages and/or genders based on the systolic blood pressure data, the pulse wave transit time, the body mass indexes and the ages and/or genders. The diastolic blood pressure model establishment module is further configured to establish a diastolic blood pressure model indicative of a relationship between the diastolic blood pressures and the pulse wave intensity ratios, the body mass indexes and the ages and/or genders based on the diastolic blood pressure data, the pulse wave intensity ratios, the body mass indexes and the ages and/or genders.

In an embodiment, the systolic blood pressure model establishment module is configured to establish the systolic blood pressure model through regression analysis by combining the pulse wave transit time, the body mass indexes and the ages and/or genders of the plurality of subjects to be examined with the systolic blood pressure data of the plurality of subjects to be examined. In an embodiment, the systolic blood pressure model establishment module is configured to establish the systolic blood pressure model by using a least squares regression method.

In an embodiment, the diastolic blood pressure model establishment module is configured to establish the diastolic blood pressure model through regression analysis by combining the pulse wave intensity ratios, the body mass indexes and the ages and/or genders of the plurality of subjects to be examined with the diastolic blood pressure data of the plurality of subjects to be examined. In an embodiment, the diastolic blood pressure model establishment module is configured to establish the diastolic blood pressure model by using a least squares regression method.

In an embodiment of the present disclosure, the apparatus 800 further comprises a grouping module configured to divide the plurality of subjects to be examined into a plurality of groups based on the ages and/or genders. Further, the systolic blood pressure model establishment module is further configured to: for each of the plurality of groups, establish a systolic blood pressure model for the group indicative of a relationship between systolic blood pressures and pulse wave transit time and body mass indexes of subjects to be examined included in the group based on systolic blood pressure data, the pulse wave transit time and the body mass indexes; and the diastolic blood pressure model establishment module is further configured to: for each of the plurality of groups, establish a diastolic blood pressure model for the group indicative of a relationship between diastolic blood pressures and pulse wave intensity ratios, and body mass indexes of subjects to be examined included in the group based on diastolic blood pressure data, the pulse wave intensity ratios and the body mass indexes.

In an embodiment of the present disclosure, when a systolic blood pressure model is established, the systolic blood pressure model establishment module comprises a first training set unit configured to construct a first training set comprising the systolic blood pressure data, the pulse wave transit time and the body mass indexes of the plurality of subjects to be examined; and a parameter determination unit configured to determine parameters in the systolic blood pressure model by using the first training set with the pulse wave transit time and the body mass indexes being inputs of the systolic blood pressure model and the systolic blood pressures being an output of the systolic blood pressure model. In an embodiment, the parameter determination unit is configured to determine the parameters through regression analysis by combining the pulse wave transit time and the body mass indexes of the plurality of subjects to be examined with the systolic blood pressure data of the plurality of subjects to be examined. In an embodiment, the parameter determination unit is configured to determine the parameters by using a least squares regression method.

In an embodiment of the present disclosure, the diastolic blood pressure model establishment module comprises a second training set unit configured to construct a second training set comprising the diastolic blood pressure data, the pulse wave intensity ratios and the body mass indexes of the plurality of subjects to be examined; and a parameter determination unit configured to determine parameters in the diastolic blood pressure model by using the second training set with the pulse wave intensity ratios and the body mass indexes being inputs of the diastolic blood pressure model and the diastolic blood pressures being an output of the diastolic blood pressure model. In an embodiment, the parameter determination unit is configured to determine the parameters through regression analysis by combining the pulse wave intensity ratios and the body mass indexes of the plurality of subjects to be examined with the diastolic blood pressure data of the plurality of subjects to be examined. In an embodiment, the parameter determination unit is configured to determine the parameters by using a least squares regression method.

Figure 9:
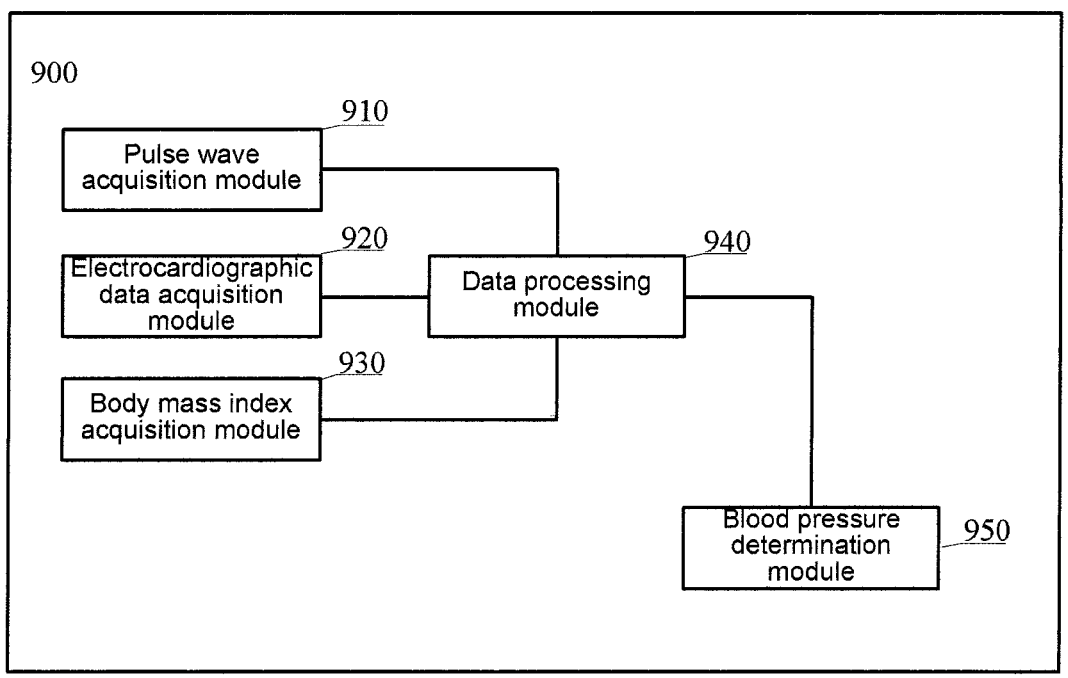
FIG. 9 illustrates a diagram of an apparatus for determining a blood pressure of a subject to be examined according to an exemplary embodiment of the present disclosure.

FIG. 9 illustrates a diagram of an apparatus 900 for determining a blood pressure of a subject to be examined according to an embodiment of the present disclosure. As shown in FIG. 9, the apparatus 900 comprises a pulse wave acquisition module 910, an electrocardiographic data acquisition module 920, a body mass index acquisition module 930, a data processing module 940 and a blood pressure determination module 950.

The pulse wave acquisition module 910 is configured to acquire pulse wave data of the subject to be examined. In an embodiment, the pulse wave data is manually input by the subject to be examined or an operator. In another embodiment, the pulse wave data is measured by a measurement device, wherein measurement device is for example a pulse wave sensor, such as, a photoelectric sensor.

The electrocardiographic data acquisition module 920 is configured to acquire electrocardiographic data of the subject to be examined. In an embodiment, the electrocardiographic data is manually input by the subject to be examined or an operator. In another embodiment, the electrocardiographic data is measured by a measurement device, wherein measurement device is for example an electrocardiogram sensor, such as, a dry electrode.

The body mass index acquisition module 930 is configured to acquire a body mass index of the subject to be examined. In an embodiment, the body mass index is manually input by the subject to be examined or an operator. In another embodiment, the body mass index is calculated according to a height and a weight of the subject to be examined which are measured by a measurement device. The body Mass Index (BMI) is a square of the weight (W) of the subject to be examined divided by the height (L) of the subject to be examined, wherein the weight is in kilograms and the height is in meters.

The data processing module 940 is configured to determine pulse wave transit time and a pulse wave intensity ratio based on the pulse wave data and the electrocardiographic data. In an embodiment, the pulse wave data comprises time of a maximum slope point of a pulse wave, a peak value of the pulse wave, and a trough value of the pulse wave, and the electrocardiographic data comprises time of a peak of an electrocardiogram. In this embodiment, the data processing module 940 is configured to calculate the pulse wave transit time according to the time of the maximum slope point of the pulse wave and the time of the peak of the electrocardiogram. Specifically, the pulse wave transit time is a difference between the time of the maximum slope point of the pulse wave and the time of the peak of the electrocardiogram. In an embodiment, the pulse wave data comprises time of a maximum slope point of a pulse wave, a peak value of the pulse wave, and a trough value of the pulse wave, and the electrocardiographic data comprises time of a peak of an electrocardiogram. In this embodiment, the data processing module 940 is configured to calculate the pulse wave intensity ratio according to the peak value and the valley value of the pulse wave, and specifically the pulse wave intensity ratio is a ratio of the peak value of the pulse wave to the valley value of the pulse wave.

The blood pressure determination module 950 is configured to determine the blood pressure including a systolic blood pressure and a diastolic blood pressure of the subject to be examined according to a pre-established blood pressure model based on the pulse wave transit time, the pulse wave intensity ratio and the body mass index. Specifically, the pre-established blood pressure model is, for example, the systolic blood pressure model and the diastolic blood pressure model established in steps S130 and S140 disclosed above, such as equations 1 and 2 shown above. Obviously, the blood pressure determination module 940 can easily use the equations 1 and 2 to calculate the systolic blood pressure and the diastolic blood pressure of the subject to be examined based on the pulse wave transit time, the pulse wave intensity ratio and the body mass index.

In an embodiment of the present disclosure, the apparatus 900 for determining a blood pressure of a subject to be examined further comprises: an age and gender acquisition module, configured to acquire an age and/or gender of the subject to be examined. In an embodiment, the age and/or gender is input manually by the subject to be examined or an operator.

In an embodiment, the blood pressure determination module 940 is further configured to determine the systolic blood pressure and the diastolic blood pressure of the subject to be examined according to a pre-established blood pressure model based on the pulse wave transit time, the pulse wave intensity ratio, the body mass index and the age and/or gender. Specifically, the pre-established blood pressure model is, for example, the systolic blood pressure model and the diastolic blood pressure model established in steps S340 and S350 disclosed above, such as equations 3 and 4 shown above. Obviously, the blood pressure determination module 940 can easily use the equations 3 and 4 to calculate the systolic blood pressure and the diastolic blood pressure of the subject to be examined based on the pulse wave transit time, the pulse wave intensity ratio, the body mass index, and the age.

In an embodiment of the present disclosure, the apparatus 900 for determining a blood pressure of a subject to be examined further comprises: a model selection module configured to select a blood pressure model suitable for the age and/or gender of the subject to be examined from a plurality of pre-established blood pressure models according to the age and/or gender. Here, the plurality of pre-established blood pressure models are applicable to certain age ranges and/or genders, respectively.

In an embodiment, the blood pressure determination module 940 is further configured to determine the systolic blood pressure and the diastolic blood pressure of the subject to be examined according to the selected blood pressure model based on the pulse wave transit time, the pulse wave intensity ratio and the body mass index.

In an embodiment of the present disclosure, the apparatus 900 for determining a blood pressure of a subject to be examined further comprises an update module configured to acquire a new blood pressure model from a remote server and replace a current blood pressure model with the new blood pressure model. The remote server may comprise or be coupled to the apparatus 800 for establishing a blood pressure model as shown in FIG. 8.

Figure 10:
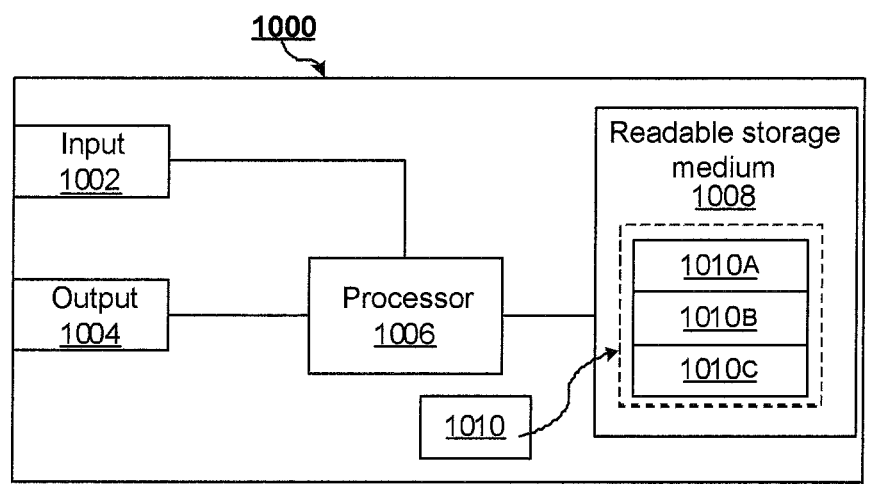
FIG. 10 illustrates a hardware arrangement of an apparatus according to an exemplary embodiment of the present disclosure.

FIG. 10 is a block diagram illustrating an exemplary hardware arrangement 1000 of the apparatus 800 shown in FIG. 8 or the apparatus 900 shown in FIG. 9 according to an embodiment of the present disclosure. The hardware arrangement 1000 comprises a processor 1006 (for example, a Digital Signal Processor (DSP) or a Central Processing Unit (CPU)). The processor 1006 may be a single processing unit or a plurality of processing units for performing different actions of the flows described herein. The arrangement 1000 may further comprise an input unit 1002 for receiving signals from other entities, and an output unit 1004 for providing signals to other entities. The input unit 1002 and the output unit 1004 may be arranged as a single entity or separate entities. In some embodiments, the input unit 1002 may be, for example, a keyboard, a mouse, a trackball, a touch screen etc. of the apparatus 800 or 900, or in other embodiments, the input unit 1002 may be, for example, the electrocardiogram sensor, the pulse wave sensor etc., or in still other embodiments, the input unit 1002 may be, for example, an interface for interacting with the input device etc. (in other words, the input unit 1002 may be an optional part of the hardware arrangement 1000). In some embodiments, the output unit 1004 may be, for example, a display, a printer, a speaker, etc. of the apparatus 800 or 900, or, in other embodiments, the output unit 1004 may be, for example, an interface for interacting with the output device etc. (in other words, the output unit 1004 may also be an optional part of the hardware arrangement 1000).

In addition, the arrangement 1000 may comprise at least one readable storage medium 1008 in a form of nonvolatile or volatile memory, such as an Electrically Erasable Programmable Read Only Memory (EEPROM), a flash memory, and/or a hard disk drive. The readable storage medium 1008 comprises a computer program 1010 which includes codes/computer readable instructions that, when executed by the processor 1006 in the arrangement 1000, cause the hardware arrangement 1000 and/or the apparatus 800 or the apparatus 900 including the hardware arrangement 1000 to perform, for example, the flows described above in connection with FIGS. 1 to 7 and any variations thereof.

The computer program 1010 may be configured with computer program codes having, architecture of for example, computer program modules 1010A-1010C. Thus, in an exemplary embodiment when using the hardware arrangement 1000 in, for example, the apparatus 800, the codes in the computer program of the arrangement 1000 comprise a module 1010A configured to acquire pulse wave data, electrocardiographic data, blood pressure data and body mass indexes of a plurality of subjects to be examined. The codes in the computer program further comprise a module 1010B configured to determine pulse wave transit time and pulse wave intensity ratios based on the pulse wave data and the electrocardiographic data. The codes in the computer program further comprise a module 1010C configured to establish the blood pressure model based on one or more of the blood pressure data, the pulse wave transit time, the pulse wave intensity ratios, and the body mass indexes of the plurality of subjects to be examined.

In addition, in the exemplary embodiment when using the hardware arrangement 1000 in, for example, the apparatus 900, the codes in the computer program of the arrangement 1000 comprise a module 1010A configured to acquire pulse wave data, electrocardiographic data and a body mass index of a subject to be examined. The codes in the computer program further comprise a module 1010B configured to determine pulse wave transit time and a pulse wave intensity ratio based on the pulse wave data and the electrocardiographic data. The codes in the computer program further comprise a module 1010C configured to determine a blood pressure of the subject to be examined based on a pre-established blood pressure model based on the pulse wave transit time, the pulse wave intensity ratio and the body mass index.

The computer program module may substantially perform various actions in the flows shown in FIGS. 1 to 7 to simulate the apparatus 800 or the apparatus 900. In other words, when different computer program modules are executed in the processor 1006, they may correspond to the different modules or units described above in the apparatus 800 or 900.

Although the code means in the embodiments disclosed above in connection with FIG. 10 is implemented as a computer program module, which when executed in the processor 1006, causes the hardware arrangement 1000 to perform the actions described above in connection with FIGS. 1 to 7, in alternative embodiments, at least one of the code means may be at least partially implemented as a hardware circuit.

The processor may be a single Central Processing Unit (CPU), or may also comprise two or more processing units. For example, the processor may comprise a general purpose microprocessor, an instruction set processor, and/or a related chipset and/or a dedicated microprocessor (for example, an Application Specific Integrated Circuit (ASIC)). The processor may also comprise an onboard memory for buffering purposes. The computer program may be carried by a computer program product connected to the processor. The computer program product may comprise a computer-readable medium having a computer program stored thereon. For example, the computer program product may be a flash memory, a Random Access Memory (RAM), a Read Only Memory (ROM), or an EEPROM, and in alternative embodiments, the computer program module described above may be distributed into different computer program products in a form of memory within the UE.

By using the method and apparatus for establishing a blood pressure model according to some embodiments of the present disclosure, it is possible to more effectively establish a blood pressure model for a group including a large number of individuals. In addition, when the blood pressure model is established, not only the pulse wave data and the electrocardiographic data are considered, but also data such as the body mass indexes and the ages and/or genders is considered, which can establish a blood pressure model suitable for a group, thereby improving the accuracy of the blood pressure model. Further, based on the established blood pressure model, it is possible to more simply detect the blood pressure of the subject to be examined in real time.

While various embodiments of the present disclosure have been illustrated in the accompanying drawings and have been set forth in the foregoing detailed description, it is to be understood that the present disclosure is not limited to the disclosed embodiments, and many re-deployments, modifications and alternatives can be made without departing from the disclosure as defined in the following claims.

I claim:

1. A method for establishing a blood pressure model, comprising:
    acquiring pulse wave data, electrocardiographic data, blood pressure data, and body mass indexes of a plurality of subjects to be examined, wherein the blood pressure data comprises systolic blood pressure data and diastolic blood pressure data;
    determining pulse wave transit time and pulse wave intensity ratios based on the pulse wave data and the electrocardiographic data;
    establishing a systolic blood pressure model indicative of a relationship between systolic blood pressures and the pulse wave transit time and the body mass indexes at least based on the systolic blood pressure data, the pulse wave transit time, and the body mass indexes; and
    establishing a diastolic blood pressure model indicative of a relationship between diastolic blood pressures and the pulse wave intensity ratios and the body mass indexes at least based on the diastolic blood pressure data, the pulse wave intensity ratios, and the body mass indexes;
    wherein the systolic blood pressure model and the diastolic blood pressure model constitute the blood pressure model.

2. The method according to claim 1, further comprising:
    acquiring ages and/or genders of the plurality of subjects to be examined;
    wherein the step of establishing the systolic blood pressure model further comprises: establishing the systolic blood pressure model indicative of a relationship between the systolic blood pressures and the pulse wave transit time, the body mass indexes, and the ages and/or genders based on the systolic blood pressure data, the pulse wave transit time, the body mass indexes, and the ages and/or genders of the plurality of subjects to be examined; and
    wherein the step of establishing the diastolic blood pressure model further comprises: establishing the diastolic blood pressure model indicative of a relationship between the diastolic blood pressures and the pulse wave intensity ratios, the body mass indexes, and the ages and/or genders based on the diastolic blood pressure data, the pulse wave intensity ratios, the body mass indexes, and the ages and/or genders of the plurality of subjects to be examined.

3. The method according to claim 1, further comprising:
acquiring ages and/or genders of the plurality of subjects to be examined;
dividing the plurality of subjects to be examined into a plurality of groups based on the ages and/or genders;
for each of the plurality of groups, establishing a corresponding part of the systolic blood pressure model for the group indicative of a relationship between systolic blood pressures and pulse wave transit time and body mass indexes of subjects to be examined included in the group based on the systolic blood pressure data, the pulse wave transit time, and the body mass indexes; and
for each of the plurality of groups, establishing a corresponding part of the diastolic blood pressure model for the group indicative of a relationship between diastolic blood pressures and pulse wave intensity ratios, and body mass indexes of subjects to be examined included in the group based on the diastolic blood pressure data, the pulse wave intensity ratios and the body mass indexes.

4. The method according to claim 1, wherein
the step of establishing the systolic blood pressure model comprises:
constructing a first training set comprising the systolic blood pressure data, the pulse wave transit time, and the body mass indexes of the plurality of subjects to be examined; and
determining parameters in the systolic blood pressure model by using the first training set with the pulse wave transit time and the body mass indexes being inputs of the systolic blood pressure model and the systolic blood pressure data being an output of the systolic blood pressure model;
and/or
wherein the step of establishing the diastolic blood pressure model comprises:
constructing a second training set comprising the diastolic blood pressure data, the pulse wave intensity ratios, and the body mass indexes of the plurality of subjects to be examined; and
determining parameters in the diastolic blood pressure model by using the second training set with the pulse wave intensity ratios and the body mass indexes being inputs of the diastolic blood pressure model and the diastolic blood pressure data being an output of the diastolic blood pressure model.

5. The method according to claim 4, wherein the parameters are determined by using a least square regression method.

6. The method according to claim 1, further comprising:
constructing a first test set comprising systolic blood pressure data, pulse wave transit time, and body mass indexes of other subjects to be examined;
calculating systolic blood pressure data by using the systolic blood pressure model with the pulse wave transit time and the body mass indexes in the first test set; and
evaluating the systolic blood pressure model based on the calculated systolic blood pressure data and the systolic blood pressure data in the first test set;
and/or the method further comprises:

constructing a second test set comprising diastolic blood pressure data, pulse wave intensity ratios and body mass indexes of other subjects to be examined;
calculating diastolic blood pressure data by using the diastolic blood pressure model with the pulse wave intensity ratios and the body mass indexes in the second test set; and
evaluating the diastolic blood pressure model based on the calculated diastolic blood pressure data and the diastolic blood pressure data in the second test set.

7. A method for determining a blood pressure of a subject to be examined, comprising:
acquiring pulse wave data, electrocardiographic data, and a body mass index of the subject to be examined;
determining pulse wave transit time and a pulse wave intensity ratio based on the pulse wave data and the electrocardiographic data; and
determining the blood pressure of the subject to be examined according to a pre-established blood pressure model based on the pulse wave transit time, the pulse wave intensity ratio, and the body mass index.

8. The method according to claim 7, further comprising:
acquiring an age and/or gender of the subject to be examined; and
determining the blood pressure of the subject to be examined according to a pre-established blood pressure model based on the pulse wave transit time, the pulse wave intensity ratio, the body mass index, and the age and/or gender.

9. The method according to claim 7, further comprising:
acquiring an age and/or gender of the subject to be examined;
selecting a blood pressure model suitable for the subject to be examined from a plurality of pre-established blood pressure models according to the age and/or gender; and
determining the blood pressure of the subject to be examined according to the selected blood pressure model based on the pulse wave transit time, the pulse wave intensity ratio, and the body mass index.

10. The method according to claim 7, wherein the blood pressure model is established by:
acquiring pulse wave data, electrocardiographic data, body mass indexes and blood pressure data of a plurality of subjects to be examined, wherein the blood pressure data comprises systolic blood pressure data and diastolic blood pressure data;
determining pulse wave transit time and pulse wave intensity ratios based on the pulse wave data and the electrocardiographic data;
establishing a systolic blood pressure model indicative of a relationship between systolic blood pressures and the pulse wave transit time and the body mass indexes based on the systolic blood pressure data, the pulse wave transit time, and the body mass index, and
establishing a diastolic blood pressure model indicative of a relationship between diastolic blood pressures and the pulse wave intensity ratios and the body mass indexes based on the diastolic blood pressure data, the pulse wave intensity ratios, and the body mass indexes,
wherein the systolic blood pressure model and the diastolic blood pressure model constitute the blood pressure model.

11. An apparatus for determining a blood pressure of a subject to be examined, comprising:
a processor;

a memory configured to store instructions that, when executed by the processor, cause the processor to perform the method according to claim 7.

12. The apparatus according to claim 11, wherein the instructions, when executed by the processor, further cause the processor to:
   acquire a new blood pressure model from a remote server and replace the current blood pressure model with the new blood pressure model.

13. The apparatus according to claim 11, further comprising:
   a pulse wave sensor coupled to the processor and configured to measure a pulse wave of the subject to be examined; and
   an electrocardiogram sensor coupled to the processor and configured to measure an electrocardiogram of the subject to be examined.

14. The apparatus according to claim 11, wherein the blood pressure model is established by:
   acquiring pulse wave data, electrocardiographic data, body mass indexes and blood pressure data of a plurality of subjects to be examined, wherein the blood pressure data comprises systolic blood pressure data and diastolic blood pressure data;
   determining pulse wave transit time and pulse wave intensity ratios based on the pulse wave data and the electrocardiographic data;
   establishing a systolic blood pressure model indicative of a relationship between systolic blood pressures and the pulse wave transit time and the body mass indexes based on the systolic blood pressure data, the pulse wave transit time, and the body mass index, and
   establishing a diastolic blood pressure model indicative of a relationship between diastolic blood pressures and the pulse wave intensity ratios and the body mass indexes based on the diastolic blood pressure data, the pulse wave intensity ratios, and the body mass indexes,
   wherein the systolic blood pressure model and the diastolic blood pressure model constitute the blood pressure model.

15. An apparatus for establishing a blood pressure model, comprising:
   a processor;
   a memory configured to store instructions that, when executed by the processor, cause the processor to:
   acquire pulse wave data, electrocardiographic data, body mass indexes and blood pressure data of a plurality of subjects to be examined, wherein the blood pressure data comprises systolic blood pressure data and diastolic blood pressure data;
   determine pulse wave transit time and pulse wave intensity ratios based on the pulse wave data and the electrocardiographic data; and
   establish a systolic blood pressure model indicative of a relationship between systolic blood pressures and the pulse wave transit time and the body mass indexes at least based on the systolic blood pressure data, the pulse wave transit time, and the body mass index, and establish a diastolic blood pressure model indicative of a relationship between diastolic blood pressures and the pulse wave intensity ratios and the body mass indexes at least based on the diastolic blood pressure data, the pulse wave intensity ratios, and the body mass indexes, wherein the systolic blood pressure model and the diastolic blood pressure model constitute the blood pressure model.

16. The apparatus according to claim 15, wherein the instructions, when executed by the processor, further cause the processor to:
   acquire ages and/or genders of the plurality of subjects to be examined;
   establish the systolic blood pressure model indicative of a relationship between the systolic blood pressures and the pulse wave transit time, the body mass indexes, and the ages and/or genders based on the systolic blood pressure data, the pulse wave transit time, the body mass indexes, and the ages and/or genders of the plurality of subjects to be examined; and
   establish the diastolic blood pressure model indicative of a relationship between the diastolic blood pressures and the pulse wave intensity ratios, the body mass indexes, and the ages and/or genders based on the diastolic blood pressure data, the pulse wave intensity ratios, the body mass indexes, and the ages and/or genders of the plurality of subjects to be examined.

17. The apparatus according to claim 15, wherein the instructions, when executed by the processor, further cause the processor to:
   acquire ages and/or genders of the plurality of subjects to be examined;
   divide the plurality of subjects to be examined into a plurality of groups based on the ages and/or genders;
   for each of the plurality of groups, establish a corresponding part of the systolic blood pressure model for the group indicative of a relationship between systolic blood pressures and pulse wave transit time and body mass indexes of subjects to be examined included in the group based on the systolic blood pressure data, the pulse wave transit time and the body mass indexes; and
   for each of the plurality of groups, establish a corresponding part of the diastolic blood pressure model for the group indicative of a relationship between diastolic blood pressures and pulse wave intensity ratios, and body mass indexes of subjects to be examined included in the group based on the diastolic blood pressure data, the pulse wave intensity ratios and the body mass indexes.

18. The apparatus according to claim 15, wherein the instructions, when executed by the processor, further cause the processor to:
   construct a first training set comprising the systolic blood pressure data, the pulse wave transit time and the body mass indexes of the plurality of subjects to be examined; and
   determine parameters in the systolic blood pressure model by using the first training set with the pulse wave transit time and the body mass indexes being inputs of the systolic blood pressure model and the systolic blood pressure data being an output of the systolic blood pressure model;
   and/or,
   the instructions, when executed by the processor, further cause the processor to:
   construct a second training set comprising the diastolic blood pressure data, the pulse wave intensity ratios and the body mass indexes of the plurality of subjects to be examined; and
   determine parameters in the diastolic blood pressure model by using the second training set with the pulse wave intensity ratios and the body mass indexes being inputs of the diastolic blood pressure model and the diastolic blood pressure data being an output of the diastolic blood pressure model.

19. The apparatus according to claim 18, wherein the instructions, when executed by the processor, further cause the processor to:
   determine the parameters using a least square regression method.

20. The apparatus according to claim 15, wherein the instructions, when executed by the processor, further cause the processor to:
   construct a first test set comprising systolic blood pressure data, pulse wave transit time and body mass indexes of other subjects to be examined;
   calculate systolic blood pressure data by using the systolic blood pressure model with the pulse wave transit time and the body mass indexes in the first test set; and
   evaluate the systolic blood pressure model based on the calculated systolic blood pressure data and the systolic blood pressure data in the first test set;
   and/or,
   the instructions, when executed by the processor, further cause the processor to:
   construct a second test set comprising diastolic blood pressure data, pulse wave intensity ratios and body mass indexes of other subjects to be examined;
   calculate diastolic blood pressure data by using the diastolic blood pressure model with the pulse wave intensity ratios and the body mass indexes in the second test set; and
   evaluate the diastolic blood pressure model based on the calculated diastolic blood pressure data and the diastolic blood pressure data in the second test set.

* * * * *